(12) United States Patent
Loewen et al.

(10) Patent No.: US 10,210,961 B2
(45) Date of Patent: Feb. 19, 2019

(54) SYSTEM AND METHOD FOR A COMMERCIAL SPENT NUCLEAR FUEL REPOSITORY TURNING HEAT AND GAMMA RADIATION INTO VALUE

(75) Inventors: Eric P. Loewen, Wilmington, NC (US); Jordan E. Hagaman, Wilmington, NC (US)

(73) Assignee: GE-HITACHI NUCLEAR ENERGY AMERICAS, LLC, Wilmington, NC (US)

(*) Notice: Subject to any disclaimer, the term of this patent is extended or adjusted under 35 U.S.C. 154(b) by 877 days.

(21) Appl. No.: 13/469,846

(22) Filed: May 11, 2012

(65) Prior Publication Data

US 2013/0301767 A1 Nov. 14, 2013

(51) Int. Cl.
| | |
|---|---|
| *G21H 5/00* | (2006.01) |
| *G21D 9/00* | (2006.01) |
| *G21F 7/015* | (2006.01) |
| *G21H 1/00* | (2006.01) |
| *A23L 3/26* | (2006.01) |
| *A61L 2/08* | (2006.01) |

(52) U.S. Cl.
CPC ............. *G21H 5/00* (2013.01); *G21D 9/00* (2013.01); *G21F 7/015* (2013.01); *G21H 1/00* (2013.01); *A23L 3/263* (2013.01); *A61L 2/081* (2013.01); *A61L 2202/24* (2013.01)

(58) Field of Classification Search
CPC ........... G21C 1/12; G21C 19/07; G21F 7/015; G21D 9/00; G21D 7/04; G21H 5/00; A61L 2/081
USPC ................................ 376/272, 273, 274, 276
See application file for complete search history.

(56) References Cited

U.S. PATENT DOCUMENTS

| | | | | |
|---|---|---|---|---|
| 2,943,986 A | * | 7/1960 | Thorpe ................... | G21C 5/123 204/157.15 |
| 3,007,859 A | * | 11/1961 | Stoops .................... | G21D 9/00 204/157.15 |
| 3,297,537 A | * | 1/1967 | Natland ................. | G21C 5/123 210/114 |

(Continued)

FOREIGN PATENT DOCUMENTS

GB 2295484 A 5/1996

OTHER PUBLICATIONS

SE Office Action dated Apr. 15, 2014 in connection with corresponding SE Patent Application No. 1350570-6.

*Primary Examiner* — Sharon M Davis
(74) *Attorney, Agent, or Firm* — Harness, Dickey & Pierce, P.L.C.

(57) ABSTRACT

A system and a method for a commercial nuclear repository that turns heat and gamma radiation from spent nuclear fuel into a valuable revenue stream. Gamma radiation from the spent nuclear fuel of the repository may be used to irradiate and sterilize food and other substances. Gamma radiation may also be used to improve the properties of target substances. Additionally, heat decay from the spent nuclear fuel of the repository may be harnessed to heat materials or fluids. The heated fluids may be used, for instance, to produce steam that may make electricity. The heating of working fluids for use in processes, such as heated fluid streams for fermentation or industrial heating, may be transported out of the repository and co-mingled with other heat input, or other fluids.

22 Claims, 4 Drawing Sheets

(56) References Cited

U.S. PATENT DOCUMENTS

| | | | | |
|---|---|---|---|---|
| 3,716,099 A * | 2/1973 | Deschamps | ............ | F02C 1/105 |
| | | | | 165/135 |
| 3,828,197 A * | 8/1974 | Boldt | ............ | G21F 5/005 |
| | | | | 250/506.1 |
| 3,866,424 A * | 2/1975 | Busey | ............ | F22B 1/02 |
| | | | | 122/32 |
| 3,911,684 A * | 10/1975 | Busey | ............ | F03G 7/00 |
| | | | | 122/32 |
| 4,040,480 A * | 8/1977 | Richards | ............ | G21F 5/10 |
| | | | | 165/104.26 |
| 4,366,114 A * | 12/1982 | Kuhnel | ............ | G21C 19/08 |
| | | | | 250/506.1 |
| 4,464,330 A * | 8/1984 | Speir et al. | ............ | 376/159 |
| 4,749,541 A * | 6/1988 | Hardin et al. | ............ | 376/261 |
| 5,512,253 A | 4/1996 | Woodbridge et al. | | |
| 5,546,436 A * | 8/1996 | Jones et al. | ............ | 376/272 |
| 5,771,265 A | 6/1998 | Montazer | | |
| 6,183,243 B1 * | 2/2001 | Snyder | ............ | G21F 5/005 |
| | | | | 250/506.1 |
| 8,670,516 B2 * | 3/2014 | Cho et al. | ............ | 376/245 |
| 2003/0179844 A1 * | 9/2003 | Filippone | ............ | G21H 1/00 |
| | | | | 376/208 |
| 2009/0161810 A1 * | 6/2009 | Sato et al. | ............ | 376/216 |
| 2010/0101783 A1 * | 4/2010 | Vinegar | ............ | E21B 43/2401 |
| | | | | 166/247 |
| 2010/0105975 A1 | 4/2010 | Baird | | |
| 2011/0286567 A1 * | 11/2011 | Singh et al. | ............ | 376/272 |

\* cited by examiner

SYSTEM AND METHOD FOR A COMMERCIAL SPENT NUCLEAR FUEL REPOSITORY TURNING HEAT AND GAMMA RADIATION INTO VALUE

BACKGROUND OF THE INVENTION

Field of the Invention

Example embodiments relate generally to a nuclear repository, and more particularly to a system and a method for turning heat and gamma radiation into value in a nuclear repository.

Related Art

Light water reactors (LWRs) produce electricity using enriched uranium. Spent nuclear fuel (SNF), which may include fission products, $^{235}$U, and $^{239}$P, is a radioactive by-product of a LWR. The conventional strategy for handling LWR SNF is to store spent material on-site at LWRs for 10-20 years (in spent nuclear fuel pools) and eventually move the SNF to off-site, long-term geologic repositories in order to protect the environment as well as the public. Generally, geologic repositories are designed to stock-pile radioactive waste in rock deep underground (for instance, in Yucca Mountain in Nevada). For instance, as shown in FIG. 1, spent nuclear fuel has conventionally been stored in reinforced underground tunnels 2. The spent nuclear fuel may be moved into the tunnel 2 on a gantry crane rail 2. The spent nuclear fuel may include pressurized water reactor waste packages 6, co-disposal waste packages (with high-level waste canisters and/or Department of Energy spent nuclear fuel canisters) 8 and boiling water reactor waste packages 10, for example. The spent nuclear fuel may be covered by a drip shield 12, to isolate the fuel from water that may contact the waste fuel and re-enter the environment through local water tables.

During the long-term storage of the spent waste fuel, gamma radiation and radioactive heat continue to be emitted for extended periods of time (lasting thousands of years). Therefore, by storing the spent nuclear fuel in long-term storage repositories, the economic value of gamma rays and decay heat is lost.

SUMMARY OF INVENTION

Example embodiments are used to turn a waste liability (spent nuclear fuel) into a valuable revenue stream. Specifically, example embodiments provide a system and a method for a commercial nuclear repository using heat and radiation from the spent nuclear fuel as inputs for commercial processes. Gamma radiation from the spent nuclear fuel may be used to irradiate and sterilize food and other substances. Gamma radiation may also be used to improve the properties of other target substances (such as cross linking polymer compounds to make larger polymer chains). Heat decay from the spent nuclear fuel may be used to harness heat energy to heat materials or fluids. The heating of fluids may be used, for instance, to form steam that may produce electricity using an organic Rankine cycle. The heating of working fluids may also be used in other processes, such as fermentation (e.g. bio fuels) or industrial heating. Heated fluids from the long-term storage repository may also be co-mingled with other heat input, or with other fluids.

BRIEF DESCRIPTION OF THE DRAWINGS

The above and other features and advantages of example embodiments will become more apparent by describing in detail, example embodiments with reference to the attached drawings. The accompanying drawings are intended to depict example embodiments and should not be interpreted to limit the intended scope of the claims. The accompanying drawings are not to be considered as drawn to scale unless explicitly noted.

DETAILED DESCRIPTION

Figure 1:
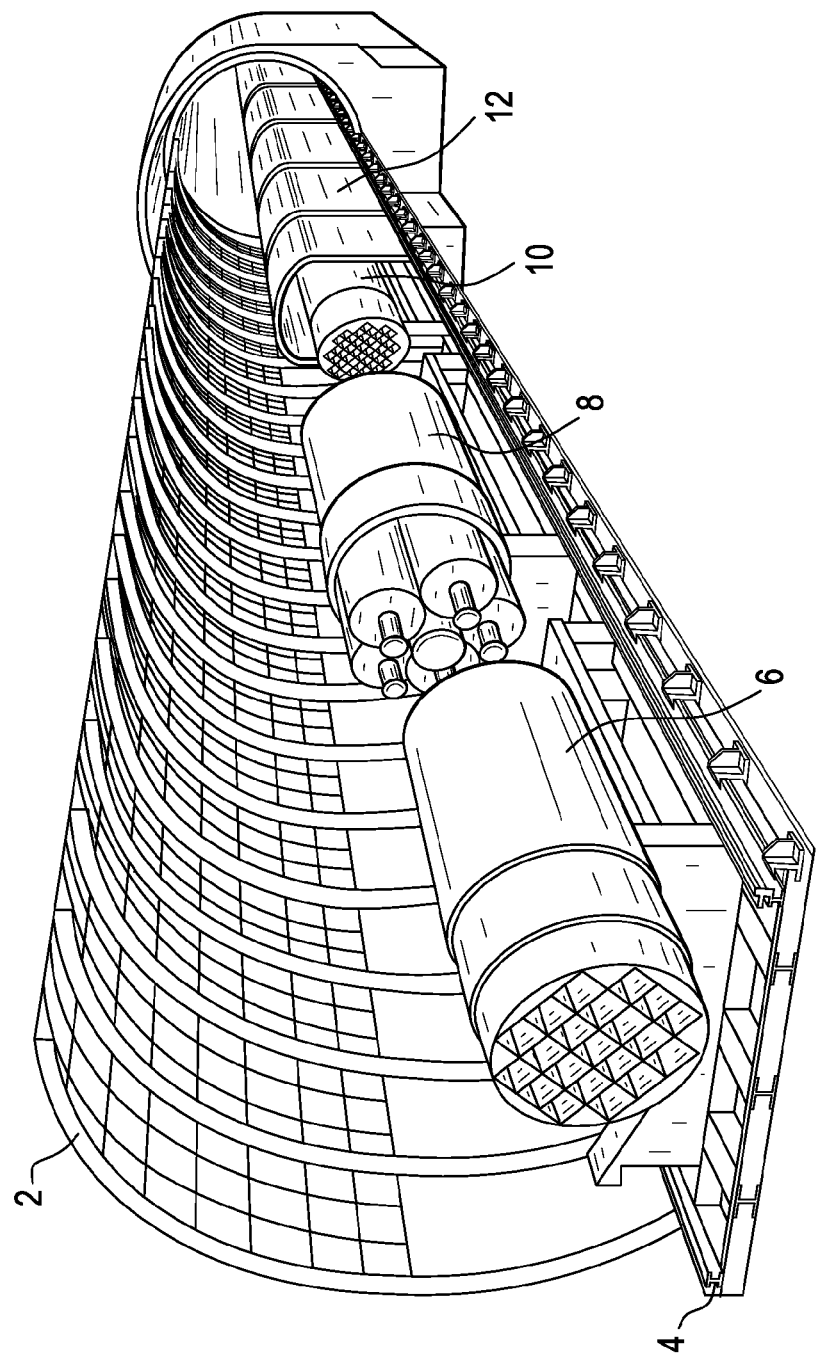
FIG. 1 is a conventional geological repository for spent nuclear fuel.

Detailed example embodiments are disclosed herein. However, specific structural and functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected" or "coupled" to another element, it may be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between", "adjacent" versus "directly adjacent", etc.).

The terminology used herein is for the purpose of describing particular embodiments only and is not intended to be limiting of example embodiments. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Figure 2:
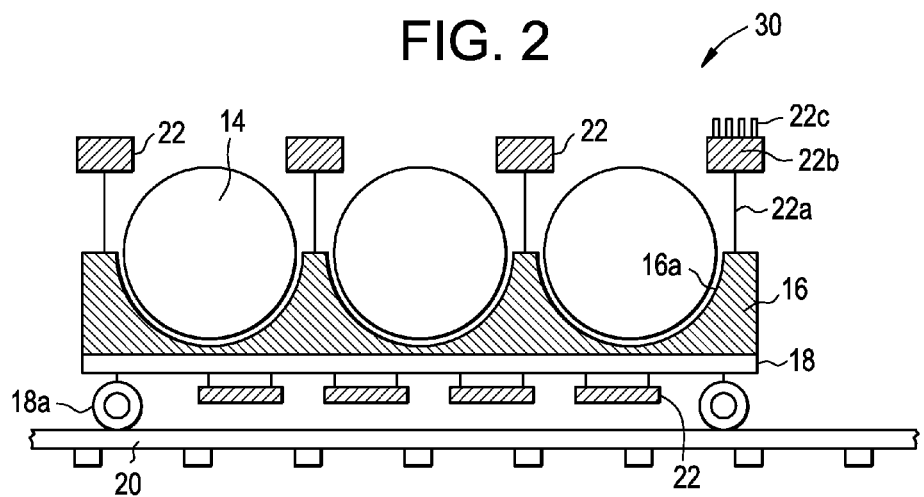
FIG. 2 is a side-view of a commercial nuclear repository configuration, in accordance with an example embodiment.

FIG. 2 is a side-view of a commercial nuclear repository configuration 30, in accordance with an example embodiment. The configuration may include spent nuclear fuel containers 14 that may be held by a support structure 16 on a rail car 18. The support structure 16 may be made of a metallic material such as stainless steel that withstands heat and radiation emitted from the spent nuclear fuel 14. The support structure 16 may include semi-circular saddles 16a that support cylindrically-shaped spent nuclear fuel containers 14. The saddles 16a may also be formed into other shapes to individually support spent nuclear fuel containers 14 that may be non-cylindrical.

Fins 22 mounted on supports 22a may be located on or near the rail car 18 to capture heat energy. Fins 22 may be made of metal (such as stainless steel) with a high heat of conductivity, to capture and magnify heat energy on and around the rail car 18. The fins 22 may be formed into flat, square or rectangular shapes. The fins 22 may also be formed into cubes, or other three-dimensional shapes. The fins 22 may include ribs 22b, or other protrusions 22c that extend from the fins 22, to increase the overall external surface area of each fin 22 (and thereby maximize heat that may be radiated from the fins 22).

In order to easily move the rail car 18 into position in a repository, such as an underground geological repository, the rail car 18 may have wheels 18a that allow the car 18 to be transported on rails 20. Alternative to using rails 20 and a rail car 18, a conveyor belt of other similar structure may be used in order to support and transport the spent nuclear fuel canisters 14 in and out of the tunnel 2.

The example embodiment shown in FIG. 2, as well as the other embodiments described herein, may make use of a constant decay heat input (and constant gamma radiation, as described in additional embodiments, below) for approximately 10 years without requiring new radioactive material to be added to the repository. Furthermore, the repositories may be continuously operated for about 30 years, with only about a 50% reduction in power output during that time. During the commercial operating life of a permanent repository, the spent nuclear fuel may be supplemented, or replaced, with new spent nuclear fuel (as needed) to optimize the repository output.

Figure 3:
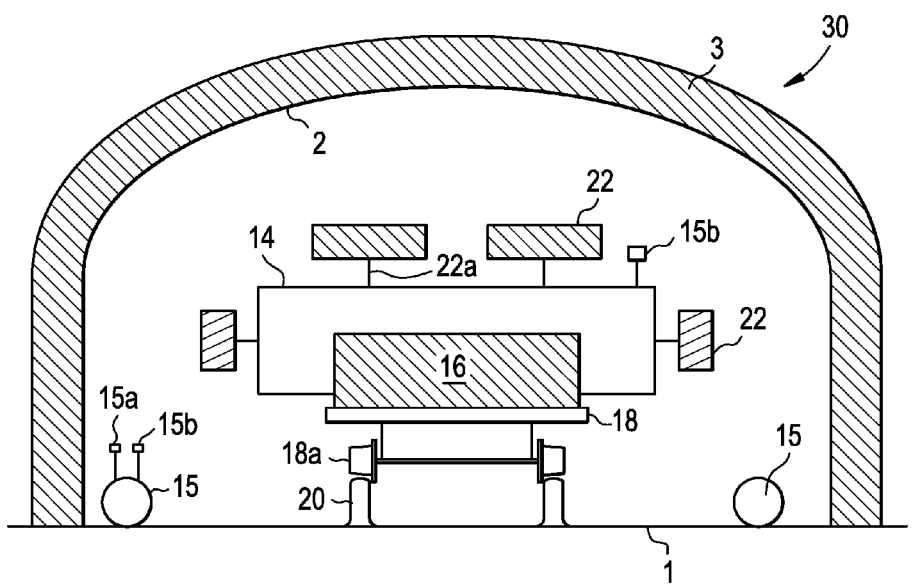
FIG. 3 is a rear-view of the commercial nuclear repository configuration of FIG. 2, in accordance with an example embodiment.

FIG. 3 is a rear-view of the commercial nuclear repository configuration 30 of FIG. 2, in accordance with an example embodiment. The repository configuration 30 may be located in a reinforced tunnel 2 that may be made of rock 3. The tunnel 2 may be, for instance, an underground tunnel 2. Alternatively, the repository 30 may be located in treatment tanks, or in other infrastructure that may be in a remote location.

The tunnel (known as a drift) 2 may include fluid piping 15. The fluid pipe 15 may include a flowing fluid, such as a liquid (for instance, water) or a gas. The pipe 15 may pass through the tunnel 2 and near rail car 18 to capture low grade heat that is emitted by both the spent nuclear fuel canisters 14 themselves, as well as the fins 22. The heated fluid piping 15 may be transported out of the repository 30 and used in commercial processes. For instance, the fluid piping 15 may be used as an input for processes requiring low grade heat, such as fermentation (e.g., to produce bio-fuels). The fluid piping 15 may also be used for industrial heating, such as a business that may wish to reduce their operating costs with an inexpensive form of heat. The fluid piping 15 may be co-mingled with other fluids, in order to heat those fluids. Alternatively, the fluid piping 15 may be used as an input to a heat exchanger that may heat other fluids. Furthermore, the fluid piping 15 may be used to produce electricity, as described herein in more detail.

It should be understood that the heat extracted by the repository 30 (both as a volumetric rate, and as a temperature) is a function of the following: the coolant (fluid in piping 15) properties, coolant flow (temperature of the fluid is inversely proportional to flow), age of the spent nuclear fuel (the greater the age, the less heat output), the matrix (physical configuration) of the spent nuclear fuel and fluid piping 15 locations, and the density and composition of the spent nuclear fuel. Therefore, the heat extracted by the fluid piping 15 (as a function of a volumetric rate of heat removal, or as a function of temperature of the coolant in the piping 15) may be controlled by: changing the coolant used in piping 15, changing a flow-rate of the coolant, tracking the age of the spent nuclear fuel, adjusting the locations of the spent nuclear fuel in proximity to the fluid piping 15, adjusting the overall amount of spent nuclear fuel canisters 14 in the drift 2, and tracking the composition (types of fission products) of the spent nuclear fuel included in the spent nuclear fuel canisters 14. For a general understanding of the repository 30 capabilities, if the fluid in piping 15 were to be water, a well designed drift 2 may create fluid output temperatures in a range of 212 to 482° F. (100 to 250° C.). Drifts 2 may be placed in parallel or in series with other drifts 2, to optimize volumetric flow or temperature ranges for the fluid piping 15, as needed. A flow meter 15a and a temperature gauge 15b may be included within the fluid piping 15, in order to control the volumetric heat removal and/or control the temperature of the coolant exiting the fluid piping 15 as it exits the drift 2. A temperature gauge 15b may also be placed in the drift 2 and near the spent nuclear fuel canisters 14 in order to further control the heating of the fluid piping 15.

Figure 4:
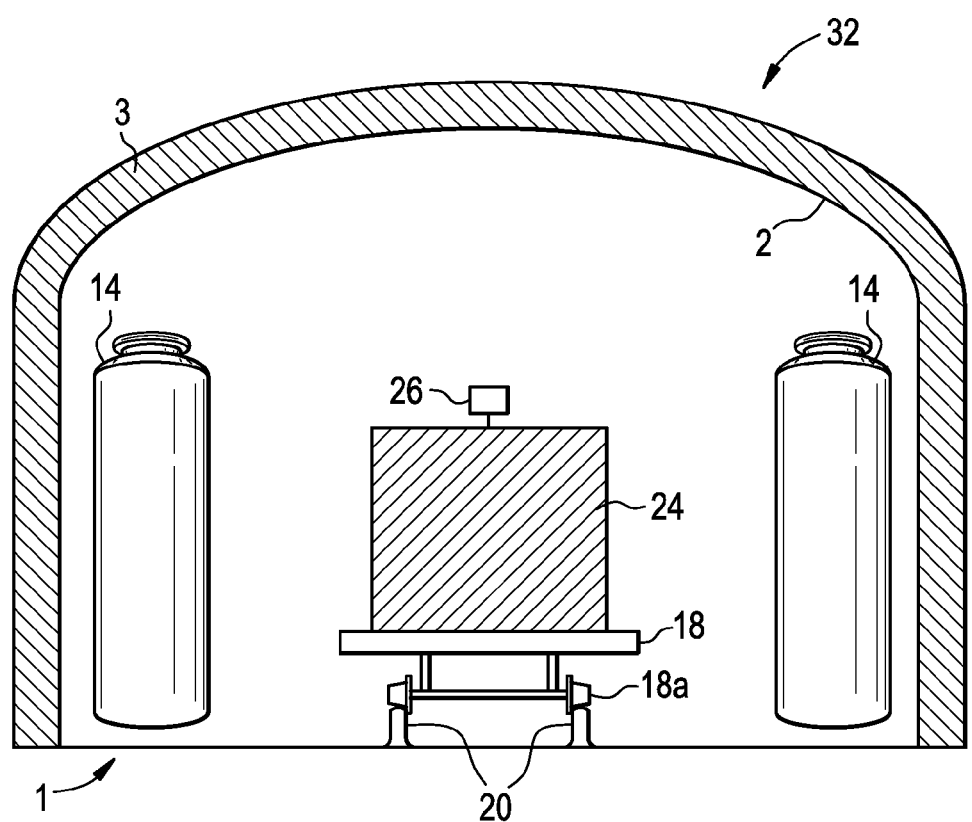
FIG. 4 is another commercial nuclear repository configuration, in accordance with an example embodiment.

FIG. 4 is another commercial nuclear repository configuration 32, in accordance with an example embodiment. The configuration may also be located in an underground tunnel 2 of rock 3 (or in another remote, protected location). The configuration 32 may include a rail car 18 with wheels 18a on a track 20 that support a target material 24. This allows the target material 24 to be easily moved in and out of the tunnel 2 with a minimal amount of radiation exposure to repository personnel. Alternative to using rails 20 and a rail car 18, a conveyor belt of other similar structure may be used in order to support and transport the target material 24 in and out of the tunnel 2.

Spent nuclear fuel canisters 14 may also be located in the tunnel 2. The spent nuclear fuel canisters 14 may emit gamma radiation that may be used to sterilize, or otherwise affect a physical property of the target material 24. Such sterilization may be used, for instance, to kill bacteria or assist in the preservation of food products, medical instruments, or other such sterilization needs. Gamma radiation from the spent nuclear fuel canisters 14 may also be used to change the chemical structure of the target material 24. For instance, gamma radiation may be used to cross link polymers in order to make larger polymers to produce consumer products.

A radiation monitor 26 may be placed near the target 24, providing operating personnel with a means of remotely monitoring the amount of radiation exposure the target 24 is receiving. The radiation monitor 26 may be attached to the target, itself, in order to accurately measure the entire amount of radiation the target 24 receives while in the tunnel 2.

It should be understood that the maximum gamma field of the tunnel (drift) 2 may be determined by the mass of fission products in the spent nuclear fuel 14, and the amount of shielding in the tunnel 2. Generally, over 700 fission products are present in typical spent nuclear fuel 14 derived from a LWR. Each of the fission products has different decay constants, concentrations, and gamma energies. To leverage the fission products to create an effective gamma irradiation drift 2, it is best to locate the spent nuclear fuel 14 around a periphery of the drift 2, such that a target material 24 may be surrounded by the spent nuclear fuel 14. Using such a configuration, the target 24 may also be easily moved in and out of the drift 2.

It should be understood that the example embodiment of FIG. 4 (similar to the embodiment of FIG. 2) may provide a permanent and/or long-term storage of spent nuclear fuel, while effectively irradiating target materials for decades. The repository may have a commercial operating life of about 60 years (or longer), and during that period the spent nuclear fuel may be supplemented, or replaced, with new spent nuclear fuel (as needed) to optimize the repository output. It should also be understood that the gamma radiation produced by the repository 32 is a function of the following: the age of the spent nuclear fuel (the greater the age, the less heat output), the type (and consistency of fission products) of spent nuclear fuel, the matrix (physical configuration) of the spent nuclear fuel in relation to the position of the target, the amount of shielding in the drift, and the density of the spent nuclear fuel. Therefore, the gamma radiation exposure absorbed by a target material 24 may be controlled by: tracking the age of the spent nuclear fuel in the spent nuclear fuel canisters 14, tracking the composition (types of fission products) of the spent nuclear fuel in the spent nuclear fuel canisters 14, adjusting the locations of the spent nuclear fuel canisters 14 in relation to the target material 24, adjusting the shielding within the drift, and adjusting the overall mass of the spent nuclear fuel canisters 14 located in the drift 2.

Figure 5:
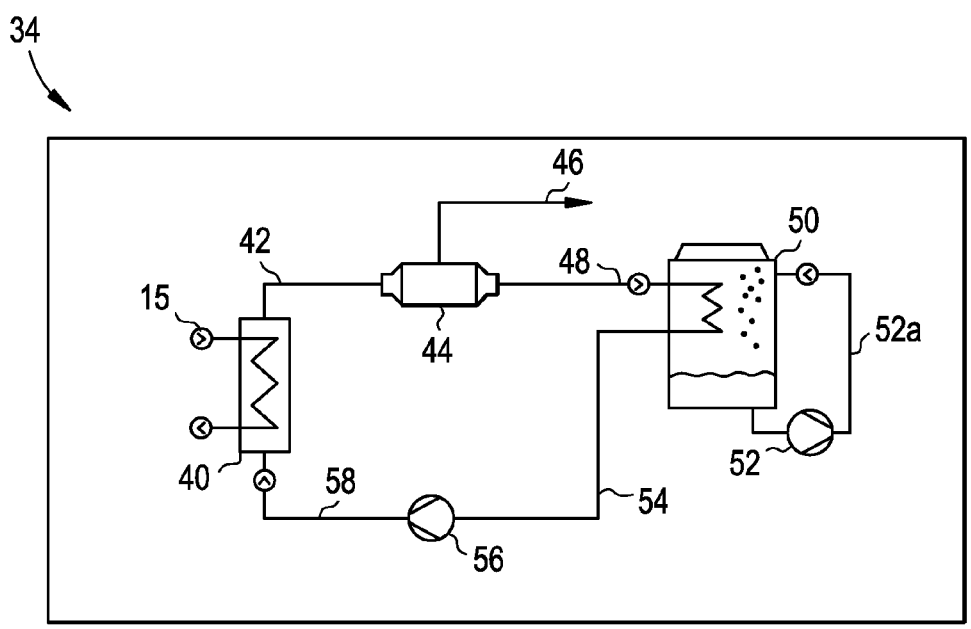
FIG. 5 is a diagram of a waste heat to electricity generator, in accordance with an example embodiment.

FIG. 5 is a diagram of a waste heat to electricity generator configuration 34, in accordance with an example embodiment. The configuration 34 may include a heat exchanger 40 that exchanges heat between heated piping 15 (of FIG. 3) and a high pressure liquid 58. The heat exchanger 40 may produce heated and pressurized vapor 42 that may be sent to an integrated power module 44 to produce electrical energy 46. Low pressure vapor 48 from the power module 44 may be sent to an evaporative condenser 50 with a recirculation pump 52 (and recirculation line 52a), to condense the vapor 48. Condensed liquid 54 may be pressurized with pump 56 to provide a complete electricity generator configuration 34. Other known configurations making use of heated piping 15 as an input to a Rankine cycle to produce electricity may also be used.

Example embodiments having thus been described, it will be obvious that the same may be varied in many ways. Such variations are not to be regarded as a departure from the intended spirit and scope of example embodiments, and all such modifications as would be obvious to one skilled in the art are intended to be included within the scope of the following claims.

What is claimed is:

1. A method of storing spent nuclear fuel, comprising:
    arranging spent nuclear fuel canisters in a drift,
    placing fluid piping in the drift,
    running coolant through the fluid piping,
    measuring at least one parameter of at least one of the drift or the coolant using at least one instrument, the at least one instrument including a flow meter, a first temperature gauge or a second temperature gauge,
    actively controlling at least one of a heat exposure rate or a radiation exposure rate of the coolant to the spent nuclear fuel canisters while the coolant is being exposed to the spent nuclear fuel canisters in the drift, to at least one of heat or irradiate the coolant,
    the actively controlling being performed at least in part based on the measured at least one parameter by,
        providing the flow meter and the first temperature gauge on the fluid piping, the measured at least one parameter including a flowrate or a first temperature of the fluid piping, and
        positioning the second temperature gauge near the spent nuclear fuel canisters in the drift, the measured at least one parameter including a second temperature near the spent nuclear fuel canisters, and
    removing the coolant from the drift.

2. The method of claim 1, further comprising:
    positioning fins around the spent nuclear fuel canisters.

3. The method of claim 2, wherein the fins are made of metal.

4. The method of claim 3, wherein the fins include one of ribs or protrusions on the fins.

5. The method of claim 1, wherein the actively controlling includes,
    adjusting at least one of an identity of the coolant, a flow-rate of the coolant, a proximity of the spent nuclear fuel canisters relative to the fluid piping, an overall quantity of spent nuclear fuel canisters, or a composition of spent nuclear fuel in the spent nuclear fuel canisters.

6. The method of claim 1, further comprising:
    supporting the spent nuclear fuel canisters on saddles located on rail cars,
    moving the spent nuclear fuel canisters into the drift via rails.

7. The method of claim 1, further comprising:
    connecting the fluid piping to a commercial process configured to utilize one of warm coolant or steam, to provide the heated coolant as an input to the commercial process.

8. The method of claim 1, wherein the coolant is water and the actively controlling includes controlling the heat exposure rate of the water, the method further comprising:
    connecting the fluid piping to a waste heat electricity generator, and
    producing electricity using the heated water.

9. The method of claim 1, wherein the arranging of the spent nuclear fuel canisters in the drift includes arranging the spent nuclear fuel canisters around the coolant.

10. The method of claim 9, wherein the at least one instrument includes a radiation monitor, the method further comprising:
    connecting the radiation monitor to the fluid piping, the measured at least one parameter being a gamma radiation exposure rate of the coolant,
    the actively controlling includes actively controlling the gamma radiation exposure rate in order to change a physical property of the coolant.

11. The method of claim 10, wherein the actively controlling includes,
adjusting at least one of a composition of spent nuclear fuel in the spent nuclear fuel canisters, a location of the spent nuclear fuel canisters in relation to the coolant, a shielding within the drift, or an overall quantity of spent nuclear fuel canisters.

12. The method of claim 1, wherein the actively controlling includes,
continuously and actively controlling the at least one of the heat exposure rate or the radiation exposure rate of the coolant to the spent nuclear fuel canisters while the coolant is being exposed to the spent nuclear fuel canisters in the drift.

13. The method of claim 1, wherein the actively controlling includes,
at least one of heating or irradiating the coolant to convert the coolant into a final product.

14. The method of claim 1, wherein the actively controlling includes,
at least one of heating or irradiating the coolant to convert the coolant into a final product with an increased economic value relative to the coolant.

15. The method of claim 1, wherein the actively controlling includes,
adjusting at least one of a proximity of the spent nuclear fuel canisters relative to the coolant, an overall quantity of spent nuclear fuel canisters, an overall quantity of the coolant, a composition of spent nuclear fuel in the spent nuclear fuel canisters, or a proximity of the coolant relative to the spent nuclear fuel canisters.

16. The method of claim 1, wherein the actively controlling coolant includes,
actively controlling a distance between the coolant and at least one of the spent nuclear fuel canisters.

17. The method of claim 16, wherein the drift is a tunnel in an underground geological repository.

18. A method of storing spent nuclear fuel, comprising:
supporting a target material in a drift on at least one of rail cars on rails or a conveyor belt,
actively controlling at least one of a heat exposure rate or a radiation exposure rate of the target material to spent nuclear fuel canisters while the target material is being exposed to the spent nuclear fuel canisters in the drift, to at least one of heat or irradiate the target material,
removing the target material from the drift, and
wherein the actively controlling of the heat exposure rate and the actively controlling of the radiation exposure rate each include moving the target material on the at least one of rail cars on rails or a conveyor belt.

19. A method of storing spent nuclear fuel, comprising:
supporting spent nuclear fuel canisters in a drift on rail cars,
actively controlling at least one of a heat exposure rate or a radiation exposure rate of a target material to the spent nuclear fuel canisters while the target material is being exposed to the spent nuclear fuel canisters in the drift, to at least one of heat or irradiate the target material,
removing the target material from the drift, and
wherein the actively controlling of the heat exposure rate and the actively controlling of the radiation exposure rate each include moving the spent nuclear fuel canisters on the rail cars.

20. A method of storing spent nuclear fuel, comprising:
arranging spent nuclear fuel canisters in a drift,
placing a target material in the drift,
actively controlling at least one of a heat exposure rate or a radiation exposure rate of the target material to the spent nuclear fuel canisters while the target material is being exposed to the spent nuclear fuel canisters in the drift, to at least one of heat or irradiate the target material, wherein the actively controlling of the at least one of the heat exposure rate or the radiation exposure rate of the target material includes actively controlling a distance between the target material and at least one of the spent nuclear fuel canisters,
removing the target material from the drift,
wherein the actively controlling of the distance between the target material and at least one of the spent nuclear fuel canisters includes using one of rail cars on rails or a conveyor belt to control the distance.

21. The method of claim 20, wherein the arranging of the spent nuclear fuel canisters in a drift includes,
supporting the spent nuclear fuel canisters on at least one of the rail cars on rails or the conveyor belt, and
moving the spent nuclear fuel canisters into the drift via at least one of the rail cars on rails or the conveyor belt.

22. A method of storing spent nuclear fuel, comprising:
arranging spent nuclear fuel canisters in a drift,
placing a target material in the drift,
actively controlling at least one of a heat exposure rate or a radiation exposure rate of the target material to the spent nuclear fuel canisters to at least one of heat or irradiate the target material,
removing the target material from the drift, and
wherein the actively controlling of the heat exposure rate and the actively controlling of the radiation exposure rate each include moving the target material on at least one of rail cars on rails or a conveyor belt.

* * * * *